US012385034B2

(12) United States Patent
Geldhof

(10) Patent No.: US 12,385,034 B2
(45) Date of Patent: Aug. 12, 2025

(54) METHODS AND APPARATUS FOR FILTRATION

(71) Applicant: ModernaTX, Inc., Cambridge, MA (US)

(72) Inventor: Benjamin Frank Geldhof, Winthrop, MA (US)

(73) Assignee: ModernaTX, Inc., Cambridge, MA (US)

( * ) Notice: Subject to any disclaimer, the term of this patent is extended or adjusted under 35 U.S.C. 154(b) by 1132 days.

(21) Appl. No.: 16/304,037

(22) PCT Filed: Jun. 21, 2017

(86) PCT No.: PCT/US2017/038498
§ 371 (c)(1),
(2) Date: Nov. 21, 2018

(87) PCT Pub. No.: WO2017/223176
PCT Pub. Date: Dec. 28, 2017

(65) Prior Publication Data
US 2020/0318098 A1    Oct. 8, 2020

Related U.S. Application Data

(60) Provisional application No. 62/354,246, filed on Jun. 24, 2016.

(51) Int. Cl.
*C12N 15/10* (2006.01)
*B01L 3/00* (2006.01)

(52) U.S. Cl.
CPC ......... *C12N 15/1017* (2013.01); *B01L 3/502* (2013.01); *B01L 3/5635* (2013.01);
(Continued)

(58) Field of Classification Search
None
See application file for complete search history.

(56) References Cited

U.S. PATENT DOCUMENTS 4,699,717 A   10/1987  Riesner et al.
4,870,015 A    9/1989  Hoffman
(Continued)

FOREIGN PATENT DOCUMENTS

CA    2028849 A1    9/1991
CA    2473135 A1    6/2003
(Continued)

OTHER PUBLICATIONS

International Search Report and Written Opinion for International Application No. PCT/US2017/038498, mailed Sep. 7, 2017 (15 pages).
(Continued)

*Primary Examiner* — Matthew D Krcha
(74) *Attorney, Agent, or Firm* — Clark & Elbing LLP

(57) ABSTRACT

The invention features methods and apparatus for concentrating a nucleic acid. Methods of the invention include providing an initial suspension of a nucleic acid and an initial liquid, contacting the initial suspension with a housing having a filter that does not pass the nucleic acid, pressurizing the housing to produce a filtrate and a nucleic acid retentate from the initial solution, and detecting the volume of the nucleic acid retentate. Apparatus of the invention include a chamber configured to hold a filter housing containing a nucleic acid suspension, a pressure source to filter the suspension, and a detector to depressurize the housing upon detecting the volume reaching a predetermined threshold. The methods and apparatus described
(Continued)

herein are useful in filtering, concentrating, and reconstituting nucleic acids, such as mRNA, in processes such as complete buffer replacement.

8 Claims, 1 Drawing Sheet

(52) U.S. Cl.
CPC . *B01L 2200/143* (2013.01); *B01L 2300/0663* (2013.01); *B01L 2300/0681* (2013.01); *B01L 2400/0487* (2013.01)

(56) References Cited

U.S. PATENT DOCUMENTS

| | | |
|---|---|---|
| 5,034,506 A | 7/1991 | Summerton et al. |
| 5,057,426 A | 10/1991 | Henco et al. |
| 5,256,294 A | 10/1993 | van Reis |
| 5,338,448 A | 8/1994 | Gjerde |
| 5,425,921 A * | 6/1995 | Coakley ............ G01N 35/1097 222/548 |
| 5,426,180 A | 6/1995 | Kool |
| 5,489,677 A | 2/1996 | Sanghvi et al. |
| 5,512,439 A | 4/1996 | Hornes et al. |
| 5,591,722 A | 1/1997 | Montgomery et al. |
| 5,599,667 A | 2/1997 | Arnold, Jr. et al. |
| 5,637,459 A | 6/1997 | Burke et al. |
| 5,639,873 A | 6/1997 | Barascut et al. |
| 5,641,400 A | 6/1997 | Kaltenbach et al. |
| 5,789,578 A | 8/1998 | Burton et al. |
| 5,808,039 A | 9/1998 | Reddy et al. |
| 5,989,911 A | 11/1999 | Fournier et al. |
| 6,011,148 A | 1/2000 | Bussey et al. |
| 6,022,715 A | 2/2000 | Merenkova et al. |
| 6,022,737 A | 2/2000 | Niven et al. |
| 6,180,778 B1 | 1/2001 | Bastian et al. |
| 6,217,899 B1 | 4/2001 | Benameur et al. |
| 6,248,268 B1 | 6/2001 | Cook |
| 6,303,378 B1 | 10/2001 | Bridenbaugh et al. |
| 6,391,542 B1 | 5/2002 | Anderson et al. |
| 6,423,492 B1 | 7/2002 | Harbron |
| 6,511,832 B1 | 1/2003 | Guarino et al. |
| 6,521,411 B2 | 2/2003 | Hecker et al. |
| 6,642,374 B2 | 11/2003 | Gjerde et al. |
| 6,812,341 B1 | 11/2004 | Conrad |
| 6,881,314 B1 | 4/2005 | Wang et al. |
| 7,026,545 B2 | 4/2006 | Barr et al. |
| 7,691,569 B2 | 4/2010 | Wohlgemuth et al. |
| 8,075,780 B2 | 12/2011 | Pearce |
| 8,093,367 B2 | 1/2012 | Kore et al. |
| 8,664,194 B2 | 3/2014 | de Fougerolles et al. |
| 8,680,069 B2 | 3/2014 | de Fougerolles et al. |
| 8,710,200 B2 | 4/2014 | Schrum et al. |
| 8,716,465 B2 | 5/2014 | Rossi et al. |
| 8,802,438 B2 | 8/2014 | Rossi et al. |
| 8,822,663 B2 | 9/2014 | Schrum et al. |
| 8,883,506 B2 | 11/2014 | Rossi et al. |
| 8,898,864 B1 | 12/2014 | Porter |
| 8,980,864 B2 | 3/2015 | Hoge et al. |
| 8,999,380 B2 | 4/2015 | Bancel et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 9,533,047 B2 | 1/2017 | de Fougerolles et al. |
| 9,675,668 B2 | 6/2017 | Bancel et al. |
| 9,803,177 B2 | 10/2017 | Rossi et al. |
| 9,814,760 B2 | 11/2017 | Bancel et al. |
| 9,850,269 B2 | 12/2017 | DeRosa et al. |
| 10,077,439 B2 | 9/2018 | Issa et al. |
| 10,285,950 B2 | 5/2019 | Frederick et al. |
| 10,493,143 B2 | 12/2019 | Ciaramella et al. |
| 10,517,940 B2 | 12/2019 | Ciaramella et al. |
| 10,543,269 B2 | 1/2020 | Ciaramella et al. |
| 10,653,767 B2 | 5/2020 | Ciaramella et al. |
| 10,675,342 B2 | 6/2020 | Ciaramella et al. |
| 10,695,419 B2 | 6/2020 | Ciaramella et al. |
| 10,702,599 B2 | 7/2020 | Ciaramella et al. |
| 10,702,600 B1 | 7/2020 | Ciaramella et al. |
| 10,716,846 B2 | 7/2020 | Ciaramella et al. |
| 10,730,924 B2 | 8/2020 | Ticho et al. |
| 10,858,647 B2 | 12/2020 | Issa et al. |
| 11,845,772 B2 | 12/2023 | Issa et al. |
| 2001/0025097 A1 | 9/2001 | Sheridan et al. |
| 2002/0001812 A1 | 1/2002 | Smith et al. |
| 2002/0016450 A1 | 2/2002 | Laugharn et al. |
| 2002/0058256 A1 | 5/2002 | Rothberg et al. |
| 2002/0062017 A1 | 5/2002 | Hecker et al. |
| 2002/0114784 A1 | 8/2002 | Li et al. |
| 2002/0130430 A1 | 9/2002 | Castor |
| 2002/0153312 A1 | 10/2002 | Gjerde et al. |
| 2003/0013646 A1 | 1/2003 | Habener et al. |
| 2003/0120035 A1 | 6/2003 | Gao et al. |
| 2003/0120065 A1 | 6/2003 | Froehler et al. |
| 2003/0170810 A1 * | 9/2003 | Vedadi ................. C07K 14/205 435/306.1 |
| 2003/0170876 A1 | 9/2003 | Widner et al. |
| 2003/0170891 A1 | 9/2003 | McSwiggen |
| 2003/0180754 A1 | 9/2003 | Bergholtz et al. |
| 2003/0180779 A1 | 9/2003 | Lofton-Day et al. |
| 2003/0207288 A1 | 11/2003 | Lewin et al. |
| 2004/0038278 A1 | 2/2004 | Tzertzinis et al. |
| 2004/0076978 A1 | 4/2004 | Verfaillie |
| 2004/0142433 A1 | 7/2004 | Padgett et al. |
| 2004/0220127 A1 | 11/2004 | Sternberg et al. |
| 2004/0224425 A1 | 11/2004 | Gjerde et al. |
| 2004/0259097 A1 | 12/2004 | De Backer et al. |
| 2004/0259240 A1 | 12/2004 | Fadden |
| 2005/0003496 A1 | 1/2005 | McGall et al. |
| 2005/0053942 A1 | 3/2005 | Kauppinen et al. |
| 2005/0130196 A1 | 6/2005 | Hofstadler et al. |
| 2005/0171333 A1 | 8/2005 | Paulsen |
| 2006/0003371 A1 | 1/2006 | Russell et al. |
| 2006/0057566 A1 | 3/2006 | Van Ness et al. |
| 2006/0058266 A1 | 3/2006 | Manoharan et al. |
| 2006/0121441 A1 | 6/2006 | Spira |
| 2006/0223081 A1 | 10/2006 | Jarrell et al. |
| 2006/0257935 A1 | 11/2006 | Takeshita et al. |
| 2007/0020678 A1 | 1/2007 | Ault-Riche et al. |
| 2007/0037148 A1 | 2/2007 | Fong et al. |
| 2007/0037770 A1 | 2/2007 | Gryaznov et al. |
| 2007/0244062 A1 | 10/2007 | Laux et al. |
| 2007/0281336 A1 | 12/2007 | Jendrisak et al. |
| 2008/0076910 A1 | 3/2008 | Takkellapati et al. |
| 2008/0153078 A1 | 6/2008 | Braman et al. |
| 2008/0171711 A1 | 7/2008 | Hoerr et al. |
| 2008/0274463 A1 | 11/2008 | Chen et al. |
| 2008/0311140 A1 | 12/2008 | Lee et al. |
| 2009/0099041 A1 | 4/2009 | Church et al. |
| 2009/0192303 A1 | 7/2009 | Skagestad |
| 2009/0215125 A1 | 8/2009 | Reed et al. |
| 2009/0264511 A1 | 10/2009 | de Fougerolles et al. |
| 2009/0270278 A1 | 10/2009 | Lim et al. |
| 2009/0286852 A1 | 11/2009 | Kariko et al. |
| 2009/0286955 A1 | 11/2009 | Hatala et al. |
| 2010/0015232 A1 | 1/2010 | Besenbacher et al. |
| 2010/0047261 A1 | 2/2010 | Hoerr et al. |
| 2010/0048883 A1 | 2/2010 | Ketterer et al. |
| 2010/0178272 A1 | 7/2010 | Hartmann et al. |
| 2010/0183639 A1 | 7/2010 | Uhlmann et al. |
| 2010/0261231 A1 | 10/2010 | Kore et al. |
| 2010/0317532 A1 | 12/2010 | Liu et al. |
| 2011/0143397 A1 | 6/2011 | Kariko et al. |
| 2011/0218170 A1 | 9/2011 | Thottassery et al. |
| 2011/0244026 A1 | 10/2011 | Guild et al. |
| 2011/0250225 A1 | 10/2011 | Fotin-Mleczek et al. |
| 2011/0281938 A1 | 11/2011 | Schaub et al. |
| 2011/0294205 A1 | 12/2011 | Hukari et al. |
| 2011/0319506 A1 | 12/2011 | Erbacher et al. |

(56) References Cited

U.S. PATENT DOCUMENTS

| | | |
|---|---|---|
| 2012/0009222 A1 | 1/2012 | Nguyen et al. |
| 2012/0046346 A1 | 2/2012 | Rossi et al. |
| 2012/0100136 A1 | 4/2012 | Patel et al. |
| 2012/0129261 A1 | 5/2012 | Eberwine et al. |
| 2012/0140097 A1 | 6/2012 | Morita et al. |
| 2012/0251618 A1 | 10/2012 | Schrum et al. |
| 2012/0309053 A1 | 12/2012 | Wellings |
| 2013/0046084 A1 | 2/2013 | Brown et al. |
| 2013/0052721 A1 | 2/2013 | Hollander et al. |
| 2013/0058894 A1 | 3/2013 | Maldonado et al. |
| 2013/0115272 A1 | 5/2013 | de Fougerolles et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0197068 A1 | 8/2013 | Kariko et al. |
| 2013/0203115 A1 | 8/2013 | Schrum et al. |
| 2013/0244282 A1 | 9/2013 | Schrum et al. |
| 2013/0245103 A1 | 9/2013 | de Fougerolles et al. |
| 2013/0245106 A1 | 9/2013 | de Fougerolles et al. |
| 2013/0251618 A1 | 9/2013 | Li et al. |
| 2013/0259923 A1 | 10/2013 | Bancel et al. |
| 2013/0259924 A1 | 10/2013 | Bancel et al. |
| 2014/0010861 A1 | 1/2014 | Bancel et al. |
| 2014/0105964 A1 | 4/2014 | Bancel et al. |
| 2014/0105966 A1 | 4/2014 | Bancel et al. |
| 2014/0147454 A1 | 5/2014 | Chakraborty et al. |
| 2014/0200261 A1 | 7/2014 | Hoge et al. |
| 2014/0206752 A1 | 7/2014 | Afeyan et al. |
| 2014/0206852 A1 | 7/2014 | Hoge et al. |
| 2014/0241956 A1 | 8/2014 | Page et al. |
| 2014/0243399 A1 | 8/2014 | Schrum et al. |
| 2014/0273230 A1 | 9/2014 | Chen et al. |
| 2014/0275227 A1 | 9/2014 | Hoge et al. |
| 2014/0343129 A1 | 11/2014 | de Fougerolles et al. |
| 2014/0371302 A1 | 12/2014 | Afeyan et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0044758 A1 | 2/2015 | Amshey et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0105275 A1 | 4/2015 | Wong et al. |
| 2015/0111248 A1 | 4/2015 | Bancel et al. |
| 2015/0140120 A1 | 5/2015 | McCauley et al. |
| 2015/0141269 A1 | 5/2015 | Soldatov et al. |
| 2015/0141499 A1 | 5/2015 | Bancel et al. |
| 2015/0157781 A1 | 6/2015 | Kyle et al. |
| 2015/0166616 A1 | 6/2015 | Bancel et al. |
| 2015/0167017 A1 | 6/2015 | Roy et al. |
| 2015/0174070 A1 | 6/2015 | Cheng et al. |
| 2015/0211039 A1 | 7/2015 | Wang et al. |
| 2015/0307542 A1 | 10/2015 | Roy et al. |
| 2016/0017313 A1 | 1/2016 | Spivak et al. |
| 2016/0024139 A1 | 1/2016 | Berlanda Scorza et al. |
| 2016/0024140 A1 | 1/2016 | Issa et al. |
| 2016/0024141 A1 | 1/2016 | Issa et al. |
| 2016/0024492 A1 | 1/2016 | Issa et al. |
| 2016/0024547 A1 | 1/2016 | Bancel et al. |
| 2016/0025630 A1 | 1/2016 | Jensen et al. |
| 2016/0032273 A1 | 2/2016 | Shahrokh et al. |
| 2016/0038612 A1 | 2/2016 | Hoge et al. |
| 2016/0040154 A1 | 2/2016 | Heartlein et al. |
| 2016/0151516 A1 | 6/2016 | Bancel et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0244742 A1 | 8/2016 | Linnarsson et al. |
| 2016/0326575 A1 | 11/2016 | Von Der Mulbe et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| CN | 105087552 A | 11/2015 |
| EP | 0366400 A2 | 5/1990 |
| EP | 1083232 B1 | 2/2005 |
| EP | 1619254 A1 | 1/2006 |
| EP | 1383556 B9 | 3/2008 |
| EP | 2092064 B1 | 9/2010 |
| EP | 2377938 A1 | 10/2011 |
| EP | 2484770 A1 | 8/2012 |
| EP | 2188379 B1 | 1/2013 |
| EP | 2548960 A1 | 1/2013 |
| JP | 2008-509168 A | 3/2008 |
| JP | 2011-130725 A | 7/2011 |
| RU | 2540017 C2 | 1/2015 |
| WO | WO-91/05058 A1 | 4/1991 |
| WO | WO-93/03052 A1 | 2/1993 |
| WO | WO-93/13121 A1 | 7/1993 |
| WO | WO-97/07825 A1 | 3/1997 |
| WO | WO-98/05673 A1 | 2/1998 |
| WO | WO-00/42175 A1 | 7/2000 |
| WO | WO-01/55306 A2 | 8/2001 |
| WO | WO-01/81566 A2 | 11/2001 |
| WO | WO-02/44399 A2 | 6/2002 |
| WO | WO-03/039523 A2 | 5/2003 |
| WO | WO-03/051881 A1 | 6/2003 |
| WO | WO-2004/016803 A2 | 2/2004 |
| WO | WO-2004/020575 A2 | 3/2004 |
| WO | WO-2004/064782 A2 | 8/2004 |
| WO | WO-2005/042716 A2 | 5/2005 |
| WO | WO-2005/058933 A1 | 6/2005 |
| WO | WO-2006/015445 A1 | 2/2006 |
| WO | WO-2007/024708 A2 | 3/2007 |
| WO | WO-2007/089607 A2 | 8/2007 |
| WO | WO-2007/120863 A2 | 10/2007 |
| WO | WO-2008/045505 A2 | 4/2008 |
| WO | WO-2008/083949 A2 | 7/2008 |
| WO | WO-2008/120016 A1 | 10/2008 |
| WO | WO-2008/156829 A2 | 12/2008 |
| WO | WO-2009/016431 A1 | 2/2009 |
| WO | WO-2009/042971 A2 | 4/2009 |
| WO | WO-2009/051451 A2 | 4/2009 |
| WO | WO-2009/127060 A1 | 10/2009 |
| WO | WO-2009/127230 A1 | 10/2009 |
| WO | WO-2009/147519 A1 | 12/2009 |
| WO | WO-2009/149253 A2 | 12/2009 |
| WO | WO-2010/017510 A1 | 2/2010 |
| WO | WO-2010/109289 A1 | 9/2010 |
| WO | WO-2011/005850 A1 | 1/2011 |
| WO | WO-2011/012316 A2 | 2/2011 |
| WO | WO-2011/068810 A1 | 6/2011 |
| WO | WO-2011/071931 A2 | 6/2011 |
| WO | WO-2011/127933 A1 | 10/2011 |
| WO | WO-2011/130624 A2 | 10/2011 |
| WO | WO-2011/133868 A2 | 10/2011 |
| WO | WO-2012/019168 A2 | 2/2012 |
| WO | WO-2012/077080 A1 | 6/2012 |
| WO | WO-2012/135805 A2 | 10/2012 |
| WO | WO-2012/158736 A1 | 11/2012 |
| WO | WO-2012/164565 A1 | 12/2012 |
| WO | WO-2013/039857 A1 | 3/2013 |
| WO | WO-2013/039861 A2 | 3/2013 |
| WO | WO-2013/045434 A1 | 4/2013 |
| WO | WO-2013/052523 A1 | 4/2013 |
| WO | WO-2013/090186 A1 | 6/2013 |
| WO | WO-2013/090294 A1 | 6/2013 |
| WO | WO-2013/090648 A1 | 6/2013 |
| WO | WO-2013/096709 A2 | 6/2013 |
| WO | WO-2013/101690 A1 | 7/2013 |
| WO | WO-2013/113326 A1 | 8/2013 |
| WO | WO-2013/113501 A1 | 8/2013 |
| WO | WO-2013/113502 A1 | 8/2013 |

(56) References Cited

FOREIGN PATENT DOCUMENTS

| WO | WO-2013/130161 A1 | 9/2013 | |
|---|---|---|---|
| WO | WO-2013/151663 A1 | 10/2013 | |
| WO | WO-2013/151664 A1 | 10/2013 | |
| WO | WO-2013/151665 A2 | 10/2013 | |
| WO | WO-2013/151666 A2 | 10/2013 | |
| WO | WO-2013/151667 A1 | 10/2013 | |
| WO | WO-2013/151668 A2 | 10/2013 | |
| WO | WO-2013/151669 A1 | 10/2013 | |
| WO | WO-2013/151670 A2 | 10/2013 | |
| WO | WO-2013/151671 A1 | 10/2013 | |
| WO | WO-2013/151672 A2 | 10/2013 | |
| WO | WO-2013/151736 A2 | 10/2013 | |
| WO | WO-2013/184976 A2 | 12/2013 | |
| WO | WO-2014/028429 A2 | 2/2014 | |
| WO | WO-2014/081507 A1 | 5/2014 | |
| WO | WO-2014/093574 A1 | 6/2014 | |
| WO | WO-2014/093712 A1 | 6/2014 | |
| WO | WO-2014/093924 A1 | 6/2014 | |
| WO | WO-2014/113089 A2 | 7/2014 | |
| WO | WO-2014/144039 A1 | 9/2014 | |
| WO | WO-2014/144711 A1 | 9/2014 | |
| WO | WO-2014/144767 A1 | 9/2014 | |
| WO | WO-2014/152027 A1 | 9/2014 | |
| WO | WO-2014/152030 A1 | 9/2014 | |
| WO | WO-2014/152031 A1 | 9/2014 | |
| WO | WO-2014/152211 A1 | 9/2014 | |
| WO | WO-2014/152513 A1 | 9/2014 | |
| WO | WO-2014/152540 A1 | 9/2014 | |
| WO | WO-2014/152659 A1 | 9/2014 | |
| WO | WO-2014/152673 A1 | 9/2014 | |
| WO | WO-2014/164253 A1 | 10/2014 | |
| WO | WO-2015/006747 A2 | 1/2015 | |
| WO | WO-2015/034925 A1 | 3/2015 | |
| WO | WO-2015/034928 A1 | 3/2015 | |
| WO | WO-2015/038892 A1 | 3/2015 | |
| WO | WO-2015/048744 A2 | 4/2015 | |
| WO | WO-2015/051169 A2 | 4/2015 | |
| WO | WO-2015/051173 A2 | 4/2015 | |
| WO | WO-2015/051214 A1 | 4/2015 | |
| WO | WO-2015/058069 A1 | 4/2015 | |
| WO | WO-2015/070413 A1 | 5/2015 | |
| WO | WO-2015/085318 A2 | 6/2015 | |
| WO | WO-2015/089511 A2 | 6/2015 | |
| WO | WO-2015/101416 A1 | 7/2015 | |
| WO | WO-2015/105926 A1 | 7/2015 | |
| WO | WO-2015/179598 A2 | 11/2015 | |
| WO | WO-2015/196118 A1 | 12/2015 | |
| WO | WO-2015/196128 A2 | 12/2015 | |
| WO | WO-2015/196130 A2 | 12/2015 | |
| WO | WO-2016/011222 A2 | 1/2016 | |
| WO | WO-2016/011226 A1 | 1/2016 | |
| WO | WO-2016004311 A1 * | 1/2016 | ............ G01N 1/312 |
| WO | WO-2016/034620 A1 | 3/2016 | |
| WO | WO-2016/036902 A1 | 3/2016 | |
| WO | WO-2016/118724 A1 | 7/2016 | |
| WO | WO-2016/118725 A1 | 7/2016 | |

OTHER PUBLICATIONS

International Preliminary Report on Patentability for International Patent Application No. PCT/US2017/038498, mailed Jan. 3, 2019 (8 pages).
"Potato spindle tuber viroid," Wikipedia, <https://en.wikipedia.org/wiki/Potato_spindle_tuber_viroid>, accessed Jan. 19, 2017 (2 pages).
Anderson et al., "Incorporation of pseudouridine into mRNA enhances translation by diminishing PKR activation," Nucleic Acids Res. 38(17):5884-92 (2010).
Anderson et al., "Nucleoside modifications in RNA limit activation of 2'-5'-oligoadenylate synthetase and increase resistance to cleavage by RNase L," Nucleic Acids Res. 39(21): 9329-38 (2011) (10 pages).
Andries et al., "N1-methylpseudouridine-incorporated mRNA outperforms pseudouridine-incorporated mRNA by providing enhanced protein expression and reduced immunogenicity in mammalian cell lines and mice," J Control Release. 217:337-44 (2015).
Azarani et al., "RNA analysis by ion-pair reversed-phase high performance liquid chromatography," Nucleic Acids Res. 29(2):E7 (2001) (9 pages).
Bangs et al., "Mass Spectrometry of mRNA cap 4 from trypanosomatids reveals two novel nucleosides," J Biol Chem. 267(14):9805-15 (1992).
Bellon et al., "4'-Thio-oligo-beta-D-ribonucleotides: synthesis of β-4'-thio-oligouridylates, nuclease resistance, base pairing properties, and interaction with HIV-1 reverse transcriptase," Nucleic Acids Res. 21(7):1587-93 (1993).
Bellon et al., "Sugar modified oligonucleotides: synthesis, nuclease resistance and base pairing of oligodeoxynucleotides containing 1-(4'-thio-β-D-ribofuranosyl)-thymine," Biochem Biophys Res Commun. 184(2):797-803 (1992).
Berensmeier, "Magnetic particles for the separation and purification of nucleic acids," Appl Microbiol Biotechnol. 73:495-504 (2006).
Bhaduri et al., "Procedure for the preparation of milligram quantities of adenovirus messenger ribonucleic acid," J Virol. 10(6):1126-9 (1972).
Bynum et al., "Characterization of subcellular poly(A) RNA populations by poly(U) sepharose chromatography and discontinuous elution," Anal. Biochem. 107(2):406-16 (1980).
Carmody et al., Chapter 7: Purity and Content Analysis of Oligonucleotides by Capillary Gel Electrophoresis. *Handbook of Analysis of Oligonucleotides and Related Products*. Bonilla and Srivatsa, 243-264, retrieved from <http://www.nbchem.de/mediapool/120/1202675/data/K11050_C007.pdf> on Jul. 18, 2014 (2011).
Chen et al., "LC/MS analysis of cellular RNA reveals NAD-linked RNA," Nat. Chem. Biol. 5(12):879-81 (2009).
Chien et al., "RNA:DNA hybrids are more stable than DNA:DNA duplexes in concentrated perchlorate and trichloroacetate solutions," Nucleic Acids Res. 5(5):1627-37 (1978).
Colpan et al., "Large-scale purification of viroid RNA using $Cs_2SO_4$ gradient centrifugation and high-performance liquid chromatography," Anal. Biochem. 131(1):257-65 (1983).
Crain, "Preparation and enzymatic hydrolysis of DNA and RNA for mass spectrometry," Methods Enzymol. 193:782-90 (1990).
Cross et al., "Analysis of small nuclear ribonucleoproteins (RNPs) in *Trypanosoma brucei*: structural organization and protein components of the spliced leader RNP," Mol Cell Biol. 11(11):5516-5526 (1991).
Derrigo et al., "RNA-protein interactions in the control of stability and localization of messenger RNA (review)," Int J Mol Med. 5(2):111-23 (2000).
Dickman, "Ion Pair Reverse-Phase Chromatography: A Versatile Platform for the Analysis of RNA," <http://www.chromatographytoday.com/articles/prep-chiral-green-incsfc-gpc-ion/33/m._j._dickman/ion_pair_reverse-phase_chromatography_a_versatile_platform_for_the_analysis_of_rna/984/>, retrieved on Oct. 16, 2015 (5 pages).
Farrell, Related Techniques. RNA Methodologies: A Laboratory Guide for Isolation and Characterization. Third Edition. p. 475 (2005) (6 pages).
Farrow et al., "Combinatorial recombination of gene fragments to construct a library of chimeras," Curr Protoc Protein Sci. Chapter 26, Unit 26.2 (2010) (20 pages).
Fath et al., "Multiparameter RNA and codon optimization: a standardized tool to assess and enhance autologous mammalian gene expression," PLoS One. 6(3):e17596 (2011) (14 pages).
Gaj et al., "ZFN, TALEN, and CRISPR/Cas-based methods for genome engineering," Trends Biotechnol. 31(7):397-405 (2013).
Gilbert et al., "CRISPR-mediated modular RNA-guided regulation of transcription in eukaryotes," Cell. 154(2):442-51 (2013) (15 pages).
Gjerde et al. RNA Purification and Analysis: Sample Preparation, Extraction, Chromatography, <http://onlinelibrary.wiley.com/book/10.1002/9783527627196>, retrieved on Jul. 18, 2014 (203 pages).
Goodnow, "Pathways for self-tolerance and the treatment of autoimmune diseases," Lancet. 357(9274):2115-21 (2001).
Grosjean, Modification and editing of RNA: historical overview and important facts to remember. *Fine-Tuning of RNA Functions by Modification and Editing*. Grosjean H, 1-22 (2005).

(56) References Cited

OTHER PUBLICATIONS

Haeberli et al., "Syntheses of 4'-thioribonucleosides and thermodynamic stability and crystal structure of RNA oligomers with incorporated 4'-thiocytosine," Nucleic Acids Res. 33(13):3965-75 (2005).
Hamaguchi et al., "Direct reverse transcription-PCR on oligo(dT)-immobilized polypropylene microplates after capturing total mRNA from crude cell lysates," Clin Chem. 44(11):2256-63 (1998).
Hansen et al., "Circular RNA and miR-7 in Cancer," Cancer Res. 73(18):5609-12 (2013).
Hansen et al., "Natural RNA circles function as efficient microRNA sponges," Nature. 495(7441):384-8 (2013) (7 pages).
Henke et al., "microRNA-122 stimulates translation of hepatitis C virus RNA," EMBO J. 27(24):3300-10 (2008).
Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).
Irier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).
Jakobsen et al., "Direct mRNA Isolation Using Magnetic Oligo (dT) Beads: A Protocol for All Types of Cell Cultures, Animal and Plant Tissues," Advances in Biomagnetic Separation. ed. Uhlén et al., Eaton Publishing, 61-71 (1994) (15 pages).
Jakobsen et al., "Purification of mRNA directly from crude plant tissues in 15 minutes using magnetic oligo dT microspheres," Nucleic Acids Res. 18(12):3669 (1990).
Jani et al., "In vitro transcription and capping of Gaussia luciferase mRNA followed by HeLa cell transfection," J Vis Exp. 61:e3702 (2012) (9 pages).
Jeck et al., "Circular RNAs are abundant, conserved, and associated with ALU repeats," RNA. 19(2):141-57 (2013) (19 pages).
Kanwar et al., "Chimeric aptamers in cancer cell-targeted drug delivery," Crit Rev Biochem Mol Bio. 46(6):459-77 (2011).
Karikó et al., "Incorporation of pseudouridine into mRNA yields superior nonimmunogenic vector with increased translational capacity and biological stability." Mol Ther. 16(11):1833-40 (2008).
Karikó et al., "mRNA is an endogenous ligand for Toll-like receptor 3," J Biol Chem. 279(13):12542-50 (2004).
Karikó et al., "Suppression of RNA recognition by Toll-like receptors: the impact of nucleoside modification and the evolutionary origin of RNA," Immunity. 23(2):165-75 (2005).
Kazantsev et al., "Crystal structure of a bacterial ribonuclease P RNA," Proc Natl Acad Sci U.S.A. 102(38):13392-7 (2005).
Kim et al. "Rapid purification of RNAs using fast performance liquid chromatography (FPLC)." RNA. 13(2):289-94 (2007).
Kluiver et al., "Rapid generation of MicroRNA Sponges for MicroRNA Inhibition ," PLoS One. 7(1):E29275(2012) (8 pages).
Kore et al., "Synthesis and application of 2'-fluoro-substituted cap analogs," Bioorg Med Chem Letters. 17:5295-9 (2007).
Kormann et al., "Expression of therapeutic proteins after delivery of chemically modified mRNA in mice," Nat Biotechnol. 29(2):154-7 (including supplement) (2011) (6 pages).
Kumar et al., "Template-directed oligonucleotide strand ligation, covalent intramolecular DNA circularization and catenation using click chemistry," J Am Chem Soc. 129(21):6859-64 (2007).
Kuwahara et al., "Molecular evolution of functional nucleic acids with chemical modifications," Molecules. 15(8):5423-44 (2010).
Lapham et al., "RNase H cleavage for processing of in vitro transcribed RNA for NMR studies and RNA ligation," RNA. 2(3):289-96 (1996).
Liu et al., "Construction of circular miRNA sponges targeting miR-21 or miR-221 and demonstration of their excellent anticancer effects on malignant melanoma cells," Int J Biochem Cell Biol. 45(11):2643-50 (2013).
Liu et al., "in vitro transcription on DNA templates immobilized to streptavidin MagneSphere® paramagnetic particles," Promega Notes. 64:21 (1997) (6 pages).

Lukavsky et al., "Large-scale Preparation and Purification of Polyacrylamide-Free RNA Oligonucleotides," RNA. 10(5):889-93 (2004) (6 pages).
Maeder et al., "CRISPR RNA-guided activation of endogenous human genes," Nat Methods 10(10):977-9 (2013).
McCarthy et al., "Reversed-phase ion-pair liquid chromatography analysis and purification of small interfering RNA" Anal. Biochem. 390(2):181-8 (2009).
McKenna et al. "Purification and characterization of transcribed RNAs using gel filtration chromatography." Nat Protoc. 2(12):3270-7 (2007).
Melton et al., "Efficient in vitro synthesis of biologically active RNA and RNA hybridization probes from plasmids containing a bacteriophage SP6 promoter," Nucleic Acids Res. 12(18):7035-56 (1984).
Memczak et al., "Circular RNAs are a large class of animal RNAs with regulatory potency," Nature. 495(7441):333-8 (2013) (10 pages).
Mestas et al., "Of mice and not men: differences between mouse and human immunology," J Immunol. 172(5):2731-8 (2004).
Minuth et al., "A nucleobase analogue that pairs strongly with adenine," Angew Chem Int Ed Engl. 52(41):10874-7 (2013).
Mitra, "Using analytical ultracentrifugation (AUC) to measure global conformational changes accompanying equilibrium tertiary folding of RNA molecules," Methods in Enzymology, 2009(469):209-36 (2009).
Moretti et al., "Mechanism of translational regulation by miR-2 from sites in the 5' untranslated region or the open reading frame," RNA. 16(12):2493-502 (2010).
Mészáros et al., "Subtractive hybridization strategy using paramagnetic oligo(dT) beads and PCR," Biotechniques. 20(3):413-9 (1996).
Nielsen et al., "An mRNA is capped by a 2',5' lariat catalyzed by a group I-like ribozyme," Science. 309(5740):1584-7 (2005).
Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).
Pardi et al., "Expression kinetics of nucleoside-modified mRNA delivered in lipid nanoparticles to mice by various routes," available in PMC Nov. 10, 2016, published in final edited form as: J Control Release. 217:345-51 (2015) (18 pages).
Park et al., "Reverse transcriptase-coupled quantitative real time PCR analysis of cell-free transcription on the chromatin-assembled p21 promoter," PLoS One. 6(8):e23617 (2011) (6 pages).
Pascolo, Chapter 3: Vaccination With Messenger RNA. *Methods in Molecular Medicine*, vol. 127: DNA Vaccines: Methods and Protocols: Second Edition. Saltzman et al., Humana Press Inc., 23-40 (2006).
Pomerantz et al., "Analysis of RNA hydrolyzates by liquid chromatography-mass spectrometry," Methods Enzymol. 193:796-824 (1990).
PubChem Compound Summary for CID 262692, created Mar. 26, 2005. <URL: http://pubchem.ncbi.nlm.nih.gov/compound/262692> (11 pages).
PubChem Compound Summary for CID 479886, created Aug. 1, 2005. <URL: http://pubchem.ncbi.nlm.nih.gov/compound/479886> (12 pages).
Qiu et al., "Creating a flexible multiple microRNA expression vector by linking precursor microRNAs," Biochem Biophys Res Commun. 411(2):276-80 (2011).
Reyes-Engel et al., "Direct quantification of specific mRNA using a selected biotinylated oligonucleotide by free solution capillary electrophoresis," Nucleic Acids Res. 21(3):759-60 (1993).
Safarik et al., "Large-scale separation of magnetic bioaffinity adsorbents," Biotechnol. Lett. 23:1953-6 (2001).
Salfen et al., "Effects of exogenous ghrelin on feed intake, weight gain, behavior, and endocrine responses in weanling pigs," J Anim Sci. 82(7):1957-66 (2004).
Sasaki et al., "Construction of a normalized cDNA library by introduction of a semi-solid mRNA-cDNA hybridization system," Nucleic Acids Res. 22(6):987-92 (1994).

(56) References Cited

OTHER PUBLICATIONS

Shimelis et al., "Nuclease P1 digestion/high-performance liquid chromatography, a practical method for DNA quantitation," J Chromatogr A. 1117(2):132-6 (2006).
Slater, Chapter 16: The Purification of Poly(A)-Containing RNA by Affinity Chromatography. Methods in Molecular Biology. ed. Walker, Springer Verlag, 117-20 (1985).
Smith et al., "Purification of polynucleotide phosphorylase by affinity chromatography and some properties of the purified enzymes," Nucleic Acids Res. 1(12):1763-73 (1974).
St. Claire, "Positive ion electrospray ionization tandem mass spectrometry coupled to ion-pairing high-performance liquid chromatography with a phosphate buffer for the quantitative analysis of intracellular nucleotides," Rapid Commun Mass Spectrom. 14(17):1625-34 (2000).
Stocher et al., "Removal of Template DNA From CRNA Preparations by Combined Oligo (dT) Affinity Chromatography and DNase I Digestion," Biotechniques. 36(3):480-2 (2004).
Tavernier et al., "mRNA as gene therapeutic: how to control protein expression," J Control Release. 150(3):238-47 (2011).
Theus et al., "A simple assay for determining the capping efficiencies of RNA polymerases used for in vitro transcription," Biotechniques. 9(5):610-2, 614-5 (1990).
Valadi et al., "Exosome-mediated transfer of mRNAs and microRNAs is a novel mechanism of genetic exchange between cells," Nat Cell Biol. 9(6):654-9 (2007) (17 pages).
Vera et al., "Combination of in vitro capping and ribonuclease protection improves the detection of transcription start sites in chloroplasts," Plant Mol Biol. 19(2):309-11 (1992).
Vomelová et al., "Methods of RNA purification. All ways (should) lead to Rome," Folia Biol (Praha). 55(6):243-51 (2009).
Wang et al., "Characterization of mutation spectra with ultra-deep pyrosequencing: application to HIV-1 drug resistance," Genome Res. 17(8):1195-201 (2007).
Wang et al., "Improving the stability of aptamers by chemical modification," Curr Med Chem. 18(27):4126-38 (2011).
Wang et al., "One-step generation of mice carrying mutations in multiple genes by CRISPR/Cas-mediated genome engineering," Cell. 153(4):910-8 (2013).
Warren et al., "Highly efficient reprogramming to pluripotency and directed differentiation of human cells with synthetic modified mRNA," Cell Stem Cell. 7(5):618-30 (2010).
Weill et al., "Translational control by changes in poly(A) tail length: recycling mRNAs," Nat Struct Mol Biol. 19(6):577-85 (2012).
Weiss et al., "Prophylactic mRNA vaccination against allergy," Curr Opin Allergy Clin Immunol. 10(6):567-74 (2010) (8 pages).
Wilusz et al., "Molecular Biology. A circuitous route to noncoding RNA," Science. 340(6131):440-1 (2013).
Written Opposition for Japanese Patent Application No. 2017-049969, dated Mar. 6, 2019 (61 pages).
Xu, "Tutorial: Capillary Electrophoresis," The Chemical Educator. 1(2): 1-14 (1996) (14 pages), retrieved from <http://web.colby.edu/ch332public/files/2012/02/CE_tutorial.pdf> on Jul. 18, 2014.
Yamamoto et al., "Current prospects for mRNA gene delivery," Eur J Pharm Biopharm. 71(3):484-9 (2009).
Yanagawa et al., "Overexpression of autocrine motility factor in metastatic tumor cells: possible association with augmented expression of KIF3A and GDI-β," Lab Invest. 84(4):513-22 (2004).
Aviv et al., "Purification of Biologically Active Globin Messenger RNA by Chromatography on Oligothymidylic acid-Cellulose," Proc Nat Acad Sci USA 69(6):1408-1412 (1972).
Barendt et al., "Streamlined protocol for mRNA display," ACS Comb Sci. 15(2):77-81 (Feb. 2013).
Bryant et al., Chapter 2: Isolation of mRNA by Affinity Chromatography. *The Nucleic Acid Protocols Handbook.* Springer, 9-11 (2000) (4 pages).
Data Sheet for "Dynabeads@ mRNA Purification Kit" received Jan. 12, 2009 (2 pages).
Gilham, "The Synthesis of Polynucleotide-Celluloses and Their Use in the Fractionation of Polynucleotides," J Am Chem Soc. 86(22):4982-4985 (1964).
Häntzsch et al., "Comparison of Whole Blood RNA Preservation Tubes and Novel Generation RNA Extraction Kits for Analysis of mRNA and MiRNA Profiles." PLoS One. 1-17 (Dec. 2014).
Karikó et al., "Generating the optimal mRNA for therapy: HPLC purification eliminates immune activation and improves translation of nucleoside-modified, protein-encoding mRNA," Nucleic Acids Res. 39(21):e142, DOI: 10.1093/nar/gkr695 (2011) (10 pages).
Krieg et al., "Functional messenger RNAs are produced by SP6 in vitro transcription of cloned CDNAs," Nucleic Acids Res. 12(18):7057-70 (1984).
Nakazato et al., "Purification of messenger RNA and heterogeneous nuclear RNA containing poly(A) sequences," Methods Enzymol. 29:431-43 (1974).
Rodriguez et al., "Magnetic poly (styrene/divinylbenzene/acrylic acid)-based hybrid microspheres for bio-molecular recognition," Micro Nano Lett. 6(6):349-352 (2011).
Technical Data Sheet for "BioMag@ SelectaPure mRNA Purification System," Polysciences, Inc., dated Mar. 25, 2011 (5 page).
Zahnd et al., "Ribosome display: selecting and evolving proteins in vitro that specifically bind to a target," Nat Methods. 4(3):269-79 (Mar. 2007).

\* cited by examiner

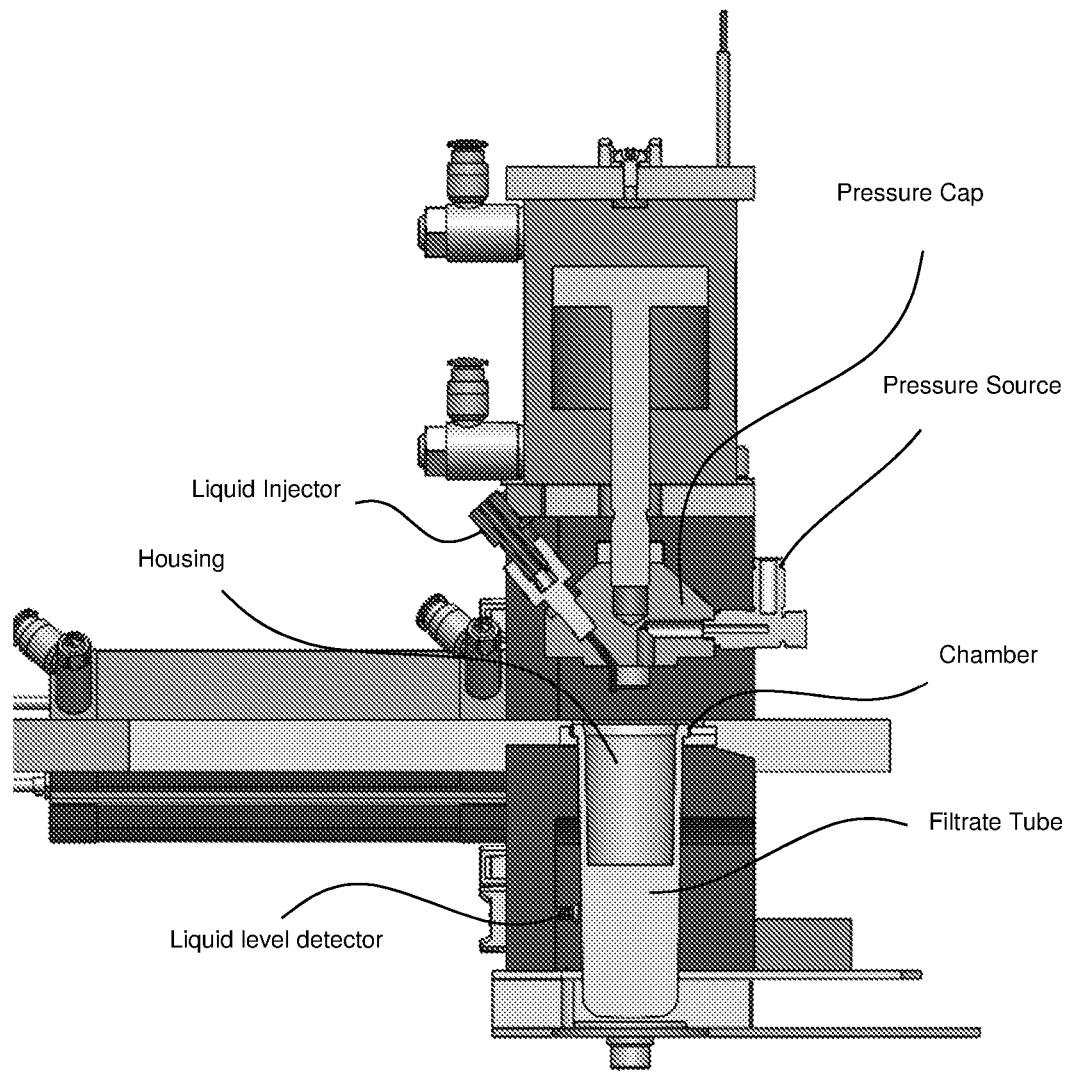

METHODS AND APPARATUS FOR FILTRATION

BACKGROUND OF THE INVENTION

Nucleic acids, such as ribonucleic acid (RNA), are being explored as therapeutic and diagnostic agents. As a result, efficient methods for processing nucleic acids are of particular interest.

Dialysis, diafiltration, and ultrafiltration can be used for processing proteins and nucleic acids. Dialysis is used for clean-up of nucleic acids for removal of low molecular weight contaminants, such as salts. However, conventional dialysis methods are performed in batches, require large amount of samples, take several hours, and incur significant sample loss. When only a small amount of sample is available, sample loss can become even more pronounced. As an alternative, ultrafiltration is based on forced separation of molecules according to size using a semipermeable membrane of a defined range of pore sizes. Ultrafiltration can be used in protein and nucleic acid purification for concentrating protein and nucleic acid molecules, changing the composition of a buffer solution, and removing low-molecular-weight solutes from these sample solutions. This technique is routinely applied in small laboratory experiments through the use of centrifugal filtration. However, centrifuge-based methods of ultrafiltration are labor intensive and time-consuming.

Thus, there remains a need for fully automated and time efficient methods and apparatus for removing contaminants from nucleic acid suspensions.

SUMMARY OF INVENTION

The present invention provides methods and apparatus for filtering and concentrating preparations of nucleic acid (e.g., RNA, e.g., mRNA).

In one aspect, the present invention provides methods of concentrating a nucleic acid by providing an initial suspension of the nucleic acid and an initial liquid; contacting the initial suspension with a housing having a filter that does not pass the nucleic acid; pressurizing the housing to produce a filtrate and a nucleic acid retentate from the initial suspension; and detecting the volume of the nucleic acid retentate. When the volume of retentate reaches a predetermined threshold, the housing depressurizes and stops the process.

In some embodiments, the method further includes injecting an additional liquid into the housing and repeating the pressurizing and detecting steps. The method includes increasing the pressure of the housing by injecting a gas (e.g., air, argon, $N_2$, or $CO_2$) into the housing. The gas can be injected, e.g., through a sealed cap. In some embodiments, the pressure of the gas within the filter housing is between about 2 bar and about 10 bar (e.g., between 2 bar and 10 bar, between 3 bar and 10 bar, between 4 bar and 9 bar, between 5 bar and 9 bar, between 6 bar and 8 bar, about 2 bar, about 3 bar, about 4 bar, about 5 bar, about 6 bar, about 7 bar, about 8 bar, about 9 bar, or about 10 bar).

The method may further include detecting the liquid level of the nucleic acid retentate within the housing. Detecting can be by capacitive sensing (e.g., using a capacitive liquid level detector).

In other embodiments, the additional liquid is different from the initial liquid. In some embodiments, the additional liquid is at least 9-fold (e.g., at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, or greater) greater than the volume of the predetermined threshold. In other embodiments, the additional liquid has a volume about equal to the difference between that of the initial suspension and the predetermined threshold. The additional liquid can be a citrate buffer (e.g., sodium citrate, such as 2 mM sodium citrate).

In some embodiments, the nucleic acid retentate has about a 10-fold greater, 11-fold greater, 12-fold greater, 13-fold greater, 14-fold greater, or 15-fold greater concentration of nucleic acid than the initial suspension.

In some embodiments, the method achieves complete buffer replacement.

The method may include a filter that has a molecular weight cutoff (MWCO) of at least 10,000 daltons (e.g., at least 10,000 daltons, at least 20,000 daltons, at least 30,000 daltons, at least 40,000 daltons, at least 50,000 daltons, at least 60,000 daltons, at least 70,000 daltons, at least 80,000 daltons, at least 90,000 daltons, at least 100,000 daltons, or greater).

In some embodiments, the nucleic acid is ribonucleic acid (RNA, e.g., messenger RNA (mRNA)). The nucleic acid can be encapsulated, e.g., in lipid nanoparticles.

In another aspect, the invention features an apparatus for concentrating nucleic acid including a chamber configured to hold a housing having a filter to hold an initial suspension of nucleic acid in contact with the filter; a pressure source configured to releasably engage and pressurize the housing to force liquid in the initial suspension through the filter to produce a filtrate and a nucleic acid retentate; and a detector configured to detect the volume of the nucleic acid retentate. The detector can be configured to depressurize the housing upon detecting the volume of the retentate reach a predetermined threshold.

In some embodiments, the chamber is configured to receive the housing provided by a user and position the housing for engagement with the pressure source.

In some embodiments, the pressure source is configured to inject a gas (e.g., air, argon, $N_2$, or $CO_2$) into the housing.

The detector can be a liquid level detector (e.g., a capacitive liquid level detector).

The apparatus may further include a liquid injector configured to inject an additional liquid (e.g., the same liquid or a different liquid from the initial liquid) into the housing. The liquid injector may be in communication with the liquid level detector.

In some embodiments, the liquid injector can be configured to inject the additional liquid into the housing upon detecting the volume of a nucleic acid retentate drop below a predetermined threshold.

The invention also provides a filtered nucleic acid suspension produced by any of the preceding methods.

BRIEF DESCRIPTION OF THE DRAWINGS

FIG. 1 is a diagram of an apparatus including a chamber holding a housing including a filter, a pressure source, a liquid level detector, and a liquid injector.

DEFINITIONS

As used herein, "pressure source" refers to an element that facilitates pressure transfer into a housing of the apparatus. A pressure source can be a line or valve that connects the housing to, e.g., an external compressed gas tank.

As used herein, "depressurize," "depressurizes," and "depressurization" refer to the change in relative pressure of the housing versus the pressure in the space separated from the housing by the filter.

The term "purified" when used in relation to a nucleic acid, refers to one that is separated from at least one contaminant or component.

As used herein, a "contaminant" is any substance which makes another unfit, impure, or inferior. Thus, a purified nucleic acid (e.g., DNA and RNA) is present in a form or setting different from that in which it is found in nature, or a form or setting different from that which existed prior to subjecting it to a treatment or purification method.

As used herein, the term "complete buffer replacement" refers to the process of exchanging at least 99% (by volume) of an initial buffer solution with a new buffer solution.

As used herein, the term "concentrating" refers to a process of decreasing the volume of the solution occupied by a substance without substantially decreasing the quantity (e.g., number of molecules or mass) of the substance. The volume of a solution is decreased, for example, by removing a liquid portion of the solution and/or by removing contaminates from (e.g., sanitizing or sterilizing) the solution.

DETAILED DESCRIPTION

The invention relates to methods and apparatus for filtering or concentrating a sample including a nucleic acid and nucleic acid suspensions filtered using the same. As an alternative to conventional dialysis, ultrafiltration provides greater efficiency in buffer exchange by enhancing filtration by force, e.g., by centrifugation, such that a retentate is isolated from the liquid and smaller soluble contaminates. The present invention provides an alternative method of ultrafiltration and/or diafiltration by providing a pressure gradient, produced other than by centrifugation, across the filter membrane. This pressure gradient drives the filtrate away from the nucleic acids retained in the pressurized housing by the filter membrane. The invention provides for automated cycles of pressurization and resuspension of the retentate, preventing the filter from drying out, which maintains the molecular integrity of the nucleic acid. Apparatus useful for performing these methods, in addition to filtered nucleic acid formulations, are also provided.

Methods

The present invention provides methods for concentrating a nucleic acid. The method includes providing an initial suspension including the nucleic acid and an initial liquid; contacting the initial suspension with a housing having a filter that does not pass the nucleic acid; pressurizing the housing to produce a filtrate and a nucleic acid retentate; and detecting the volume of the nucleic acid retentate. When the volume of the retentate reaches a predetermined threshold, the housing depressurizes, thereby concentrating the nucleic acid. Each component of this method is described in detail below.

Initial Suspension

The initial suspension can be a crude suspension of nucleic acid in a sample (e.g., having an initial liquid containing impurities from, e.g., a biological sample) or a substantially pure suspension of nucleic acid, e.g., previously purified by affinity chromatography, wherein, e.g., the suspension is to be resuspended in a different buffer, e.g., sodium citrate. The term suspension includes liquids wherein the nucleic acid is formally suspended, dissolved, or a combination thereof. The liquid of the initial suspension is herein referred to as the initial liquid.

The initial suspension may include (e.g., as part of the initial liquid) tris(hydroxymethyl)aminomethane (Tris), e.g., at a concentration of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 15 mM, 20 mM, or greater.

Additionally or alternatively, the initial suspension may also include a chelating agent. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. In some embodiments, the initial suspension includes a chelating agent (e.g., EDTA) at a concentration of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 15 mM, 20 mM, or greater.

Exemplary buffering agents that may be included as part of the initial liquid include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, and/or combinations thereof.

The initial suspension may include one or more salts (e.g., a sodium salt, a potassium salt, a magnesium salt, a lithium salt, a calcium salt, a manganese salt, a cesium salt, an ammonium salt, or an alkylammonium salt, e.g., NaCl, KCl, $MgCl_2$, $Ca^{2+}$, $MnCl_2$, and/or LiCl).

In some embodiments, the buffering agent and/or salt may be at a concentration of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 15 mM, 20 mM, or greater.

In some embodiments, the nucleic acid of the initial suspension is at a concentration from about 0.01 mg/ml to about 5 mg/ml (e.g., about 0.01 mg/ml, about 0.05 mg/ml, about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.5 mg/ml, about 3.0 mg/ml, about 3.5 mg/ml, about 4.0 mg/ml, or about 5.0 mg/ml).

The initial suspension and/or the initial liquid may have a pH of from about 3.0 to about 8.0 (e.g., of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.9, or about 8.0).

Particular examples of the initial liquid are 10 mM Tris, 1 mM EDTA, 0.5 M NaCl, 10 mM Tris, 1 mM EDTA, and 0.1 M NaCl.

Nucleic Acids

The initial suspension includes a nucleic acid (e.g., a homogeneous or heterogeneous suspension of nucleic acid, e.g., having the same or a variety of nucleic acid molecules).

In addition to nucleic acid, samples to be purified using the methods and apparatus described herein may include, for example, a surfactant (e.g., sodium dodecyl sulfate), a buffer (e.g., a sodium acetate buffer), a chelating agent (e.g., EDTA), a solvent (e.g., chloroform, ethanol, and phenol), other types of RNA (e.g., ribosomal RNA (rRNA) and transfer RNA (tRNA)), adenosine triphosphate (ATP), an enzyme (e.g., *E. coli* Poly(A) Polymerase), or any other component. In some embodiments, the sample may include components relevant to in vitro transcription reactions. In some embodiments, the sample may include components relevant to polyadenylation reactions. In some embodiments, the sample may include other types of RNA (e.g., rRNA and tRNA), e.g., of an in-vitro transcription (IVT) process.

Additionally or alternatively, nucleic acid used in the methods described herein includes nanoparticle-encapsulated nucleic acid (e.g., RNA, or mRNA encapsulated in nanoparticles (e.g., lipid nanoparticles or polymeric nanoparticles)). Nanoparticle encapsulated nucleic acid is known in the art and described, e.g., in US Publication Nos. 20130244278 and 20130244279, and in International Patent Publication No. WO 2000006120A1.

Herein, in a nucleotide, nucleoside, or polynucleotide (such as the polynucleotides of the invention, e.g., mRNA molecule), the terms "alteration" or, as appropriate, "alternative" refer to alteration with respect to A, G, U or C ribonucleotides. Generally, herein, these terms are not intended to refer to the ribonucleotide alterations in naturally occurring 5'-terminal mRNA cap moieties.

The alterations may be various distinct alterations. In some embodiments, where the polynucleotide is an mRNA, the coding region, the flanking regions and/or the terminal regions (e.g., a 3'-stabilizing region) may contain one, two, or more (optionally different) nucleoside or nucleotide alterations. In some embodiments, an alternative polynucleotide introduced to a cell may exhibit reduced degradation in the cell, as compared to an unaltered polynucleotide.

The polynucleotides of the invention can include any useful alteration, such as to the nucleobase, the sugar, or the internucleoside linkage (e.g., to a linking phosphate/to a phosphodiester linkage/to the phosphodiester backbone). In certain embodiments, alterations (e.g., one or more alterations) are present in each of the nucleobase, the sugar, and the internucleoside linkage. Alterations according to the present invention may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof. Additional alterations are described herein.

As described herein, in some embodiments, the polynucleotides of the invention do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc, and/or 3) termination or reduction in protein translation.

The polynucleotides can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, and vectors). In some embodiments, the polynucleotides may include one or more messenger RNAs (mRNAs) having one or more alternative nucleoside or nucleotides (i.e., alternative mRNA molecules). Details for these polynucleotides follow.

Nucleobase Alternatives

The alternative nucleosides and nucleotides can include an alternative nucleobase. Examples of nucleobases found in RNA include, but are not limited to, adenine, guanine, cytosine, and uracil. Examples of nucleobases found in DNA include, but are not limited to, adenine, guanine, cytosine, and thymine. These nucleobases can be altered or wholly replaced to provide polynucleotide molecules having enhanced properties, e.g., increased stability such as resistance to nucleases.

Alternative nucleotide base pairing encompasses not only the standard adenine-thymine, adenine-uracil, or guanine-cytosine base pairs, but also base pairs formed between nucleotides and/or alternative nucleotides including non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenine, cytosine, or uracil.

In some embodiments, the nucleobase is an alternative uracil. Exemplary nucleobases and nucleosides having an alternative uracil include pseudouridine ($\psi$), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5s^2U$), 5-methylaminomethyl-uracil ($mnm^5U$), 5-methylaminomethyl-2-thio-uracil ($mnm^5s^2U$), 5-methylaminomethyl-2-seleno-uracil ($mnm^5se^2U$), 5-carbamoylmethyl-uracil ($ncm^5U$), 5-carboxymethylaminomethyl-uracil ($cmnm^5U$), 5-carboxymethylaminomethyl-2-thio-uracil ($cmnm^5s^2U$), 5-propynyl-uracil, 1-propynyl-pseudouracil, 5-taurinomethyl-uracil ($\tau m^5U$), 1-taurinomethyl-pseudouridine, 5-taurinomethyl-2-thio-uracil ($\tau m^5s^2U$), 1-taurinomethyl-4-thio-pseudouridine, 5-methyl-uracil ($m^5U$, i.e., having the nucleobase deoxythymine), 1-methyl-pseudouridine ($m^1\psi$), 5-methyl-2-thio-uracil (m$^5$s$^2$U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil (m$^5$D), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil (acp$^3$U), 1-methyl-3-(3-amino-3-carboxypropyl)pseudouridine (acp$^3$ψ), 5-(isopentenylaminomethyl)uracil (inm$^5$U), 5-(isopentenylaminomethyl)-2-thio-uracil (inm$^5$s$^2$U), 5,2'-O-dimethyl-uridine (m$^5$Um), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), and 5-(isopentenylaminomethyl)-2'-O-methyl-uridine (inm$^5$Um), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the nucleobase is an alternative cytosine. Exemplary nucleobases and nucleosides having an alternative cytosine include 5-aza-cytosine, 6-aza-cytosine, pseudoisocytidine, 3-methyl-cytosine (m3C), N$_4$-acetyl-cytosine (ac4C), 5-formyl-cytosine (f5C), N$_4$-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl-adenine (m6t6A), 2-methylthio-N6-threonylcarbamoyl-adenine (ms2g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the nucleobase is an alternative guanine. Exemplary nucleobases and nucleosides having an alternative guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQ0), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

The alternative nucleobase of a nucleotide can be independently a purine, a pyrimidine, a purine or pyrimidine analog. For example, the nucleobase can be an alternative to adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Alterations on the Sugar

The alternative nucleosides and nucleotides, which may be incorporated into a polynucleotide of the invention (e.g., RNA or mRNA, as described herein), can be altered on the sugar of the nucleoside or nucleotide. In some embodiments, the alternative nucleosides or nucleotides include the structure:

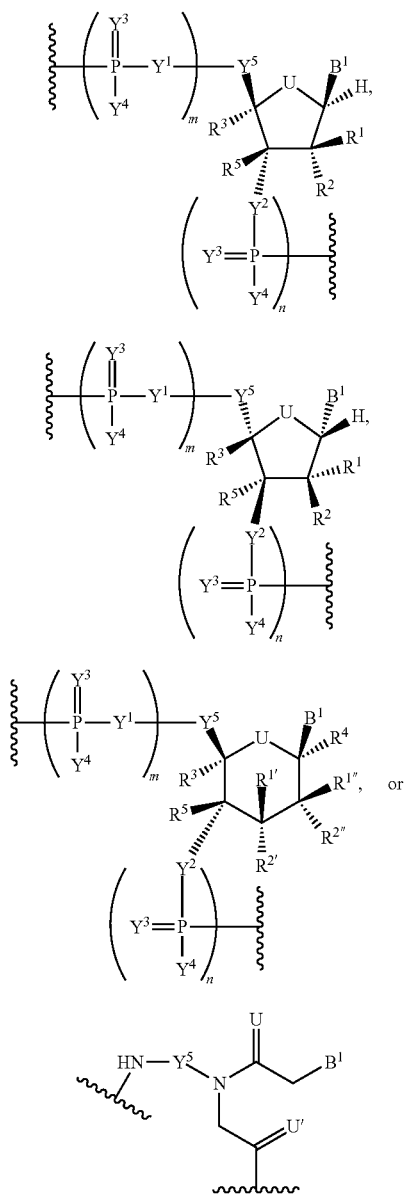

Formula II

Formula III

Formula IV

Formula V wherein $B^1$ is a nucleobase;

each U and U' is, independently, O, S, $N(R^U)_{nu}$, or $C(R^U)_{nu}$, wherein nu is 1 or 2 (e.g., 1 for $N(R^U)_{nu}$ and 2 for $C(R^U)_{nu}$) and each $R^U$ is, independently, H, halo, or optionally substituted $C_1$-$C_6$ alkyl;

each of $R^1$, $R^{1'}$, $R^{1''}$, $R^2$, $R^{2'}$, $R^{2''}$, $R^3$, $R^4$, and $R^5$ is, independently, H, halo, hydroxy, thiol, optionally substituted $C_1$-$C_6$ alkyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^3$ and/or $R^5$ can join together with one of $R^1$, $R^{1'}$, $R^{1''}$, $R^2$, $R^{2'}$, or $R^{2''}$ to form together with the carbons to which they are attached an optionally substituted $C_3$-$C_{10}$ carbocycle or an optionally substituted $C_3$-$C_9$ heterocyclyl; each of m and n is independently, 0, 1, 2, 3, 4, or 5;

each of $Y^1$, $Y^2$, and $Y^3$, is, independently, O, S, Se, —$NR^{N1}$—, optionally substituted $C_1$-$C_6$ alkylene, or optionally substituted $C_1$-$C_6$ heteroalkylene, wherein $RN'$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl; and each $Y^4$ is, independently, H, hydroxy, protected hydroxy, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, or optionally substituted amino; and $Y^5$ is O, S, Se, optionally substituted $C_1$-$C_6$ alkylene, or optionally substituted $C_1$-$C_6$ heteroalkylene;

or a salt thereof.

In some embodiments, the 2'-hydroxy group (OH) can be modified or replaced with a number of different substituents. Exemplary substitutions at the 2'-position include, but are not limited to, H, azido, halo (e.g., fluoro), optionally substituted $C_{1-6}$ alkyl (e.g., methyl); optionally substituted $C_{1-6}$ alkoxy (e.g., methoxy or ethoxy); optionally substituted $C_{6-10}$ aryloxy; optionally substituted $C_{3-8}$ cycloalkyl; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), —$O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxy is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a polynucleotide molecule can include nucleotides containing, e.g., arabinose or L-ribose, as the sugar.

In some embodiments, the polynucleotide of the invention includes at least one nucleoside wherein the sugar is L-ribose, 2'-O-methyl-ribose, 2'-fluoro-ribose, arabinose, hexitol, an LNA, or a PNA.

Alterations on the Internucleoside Linkage

The alternative nucleotides, which may be incorporated into a polynucleotide of the invention, can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl, and/or methoxy. As a non-limiting example, two non-bridging oxygens at the same position (e.g., the alpha ($\alpha$), beta ($\beta$) or gamma ($\gamma$) position) can be replaced with a sulfur (thio) and a methoxy.

The replacement of one or more of the oxygen atoms at the a position of the phosphate moiety (e.g., $\alpha$-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present invention, including internucleoside linkages which do not contain a phosphorous atom, are described herein.

Filtration

After preparation, the initial suspension is contacted with a filter, e.g., by transferring the initial suspension into a filter housing. A filter housing contains the nucleic acid throughout the duration of the filtration process (e.g., as part of the initial suspension and the retentate). The filter has an adequate pore size to prevent loss of nucleic acid from the housing. A housing may have any useful dimensions and geometry.

In some embodiments, the filter housing is suitable to hold 0.1 to 200 ml, e.g., 0.1 to 5 ml, 10 to 30 ml, or 50 to 150 ml, or about 15 ml of solution. Alternatively, a filter housing can hold about 10 ml, about 20 ml, about 25 ml, about 30 ml, about 40 ml, about 50 ml, about 60 ml, about 70 ml, about 75 ml, about 80 ml, about 90 ml, about 100 ml of liquid, or more.

Suitable housings include, but are not limited to, single-well containers having a horizontally oriented membrane (as to the direction of the filtration force) such as a CENTRICON® device available from Millipore Corporation of Billerica, Mass., single-well containers having a vertical or substantially vertically oriented membrane such as a ULTRAFREE device available from Millipore Corporation of Billerica, Mass., multiple membrane-containing single-well containers having a vertical or substantially vertically oriented membrane such as an AMICON® ULTRA™ device (e.g., Amicon 0.5, Amicon 2, Amicon 4, or Amicon 15) available from Millipore Corporation of Billerica, Mass, a VIVASPIN™ device (e.g., Vivaspin 20 or Vivaspin 100) available from GE Heathcare, or a multiwell plate such as a MULTISCREEN® plate or an ULTRACELL™ plate available from Millipore Corporation of Billerica, Mass.

Filter membranes of the invention can be any material suitable for use with a nucleic acid suspension. Representative suitable ultrafiltration membranes include those formed from polyethersulfone, polysulfone, polyimide, polyvinylidenedifluoride (PVDF), cellulose acetate, or regenerated cellulose (e.g., low-binding regenerated cellulose) such as or Vira Pure™ cellulosic ultrafiltration membranes available from Millipore Corporation, Bedford, Mass., USA.

The pore size of the filter is commonly defined by molecular weight cutoff (MWCO) and will depend on the size of the molecule to be filtered, molecular shape, electrical charge, sample concentration, sample composition, and operating conditions. Table 1 provides a general guide for selecting a MWCO for a filter of the invention according to the size of the nucleic acid.

TABLE 1

Suitable MWCO filters according to nucleic acid size.

| MWCO | Base Pairs Double Strands (DS) | Bases Single Strands (SS) |
|---|---|---|
| 1K | 5-16 | 9-32 |
| 3K | 16-32 | 32-65 |
| 5K | 25-50 | 50-95 |
| 10K | 50-145 | 95-285 |
| 30K | 145-285 | 285-570 |
| 50K | 240-475 | 475-950 |
| 100K | 475-1,450 | 950-2,900 |
| 300K | 1,450-2,900 | 2,900-5,700 |
| 1000K | 4,800-9,500 | >9,500 |

In accordance with this invention, a nucleic acid suspension is filtered with a filtration membrane to selectively retain nucleic acid molecules while permitting passage of solvent and small molecule solutes (e.g., contaminants, e.g., buffering ions) therethrough. In some embodiments, the filter has a MWCO between about 10 and about 100 kilodaltons (kD) (e.g., at least 10,000 daltons (e.g., at least 10,000 daltons, at least 20,000 daltons, at least 30,000 daltons, at least 40,000 daltons, at least 50,000 daltons, at least 60,000 daltons, at least 70,000 daltons, at least 80,000 daltons, at least 90,000 daltons, at least 100,000 daltons). In some embodiments, the MWCO is greater than 100,000 daltons.

In circumstances where nucleic acid is encapsulated in lipid nanoparticles, the guidelines given by Table 1 may underestimate the optimal molecular weight cutoff values, as encapsulation (e.g., lipid nanoparticle encapsulation) can enhance the effective size of the nucleic acid. Accordingly, it may be necessary to increase the pore size of the filter when filtering lipid nanoparticles according to the size and composition of the nanoparticles and the composition of the filtrate.

The housing can be pressurized by sealing the housing and injecting a gas into the housing. The gas can be supplied by an external tank of, e.g., compressed air, argon, $N_2$, or $CO_2$ and transferred into the housing according to known techniques (e.g., through a valve). In some embodiments, the gas is injected through a sealed cap.

Filtration occurs in response to a housing pressure between about 1 bar and about 10 bar, e.g., between 1 bar and 10 bar, between 2 bar and 10 bar, between 3 bar and 9 bar, between 5 bar and 9 bar, between 6 bar and 8 bar, about 2 bar, about 3 bar, about 4 bar, about 5 bar, about 6 bar, about 7 bar, about 8 bar, about 9 bar, or about 10 bar). In some embodiments, the pressure of the gas within the filter housing is about 7 bar. A suitable pressure is high enough to efficiently filter the suspension without rupturing the filter membrane.

When utilizing the conditions provided by any of the methods described herein, substantially complete nucleic acid retention (e.g., 90%, 91%, 92%, 93%, 94%, 95%, 96%, 97%, 98%, 99%, or 100%) can be attained over the course of filtering all or a portion of the initial liquid from the filter housing. The final volume of retentate, e.g., the threshold amount of nucleic acid suspension in the housing, can be set by the operator by, e.g., installing or configuring a liquid level detector accordingly (e.g., by attaching the liquid level sensor at a height aligned with the threshold volume).

In some embodiments, the liquid level is a detected by change in capacitance across the filter housing, e.g., by a capacitive liquid level detector. Capacitive liquid level detectors do not require contact with the inside of the housing and are thus suitable for detecting solutions containing sensitive biological materials. Capacitive liquid level detectors suitable for use as part of the present methods are known in the art and described, e.g., in U.S. Pat. No. 5,017,909. A capacitive liquid level detector of the invention can have a liquid level sensing precision of between about 10 μm and about 500 μm (e.g., 10 μm, 20 μm, 30 μm, 40 μm, 50 μm, 60 μm, 70 μm, 80 μm, 90 μm, 100 μm, 200 μm, 300 μm, 400 μm, or 500 μm). The volume associated with a height of retentate can be configured by adjusting the width of the housing at that height.

Methods of the invention feature automatic depressurization upon sensing a threshold level of retentate (e.g., a level corresponding a retentate volume between about 0.1 ml and 10 ml, e.g., about 0.1 ml, 0.2 ml, 0.3 ml, 0.4 ml, 0.5 ml, 0.6 ml, 0.7 ml, 0.8 ml, 0.9 ml, 1.0 ml, 1.1 ml, 1.2 ml, 1.3 ml, 1.4 ml, 1.5 ml, 1.6 ml, 1.7 ml, 1.8 ml, 1.9 ml, 2.0 ml, or greater). Switch mechanisms and circuitry for communication between a liquid level sensor and a pressure valve necessary for automatic depressurization are known in the art.

After the filtration step, the threshold volume of nucleic acid suspension (i.e., the retentate) is more concentrated than the initial suspension. In some embodiments, the nucleic acid retentate has about a 2-fold greater, 3-fold greater, 4-fold greater, 5-fold greater, 6-fold greater, 7-fold greater, 8-fold greater, 9-fold greater, 10-fold greater, 11-fold greater, 12-fold greater, 13-fold greater, 14-fold greater, 15-fold greater, 16-fold greater, 17-fold greater, 18-fold greater, 19-fold greater, 20-fold greater or more concentration of nucleic acid than the initial suspension. In some embodiments, the nucleic acid retentate has about a 13-fold greater concentration of nucleic acid than the initial suspension.

Refilling

The invention features a method for sequential filtering and filling (e.g., with an additional liquid) to enable complete buffer replacement (e.g., wherein the additional liquid is different from the initial liquid). In accordance with this aspect of the invention, one or more refilling steps can be performed. Overall several sequential filtration steps may be required to yield a complete buffer replacement. In some embodiments, 2, 3, 4, 5, 6, 7, 8, 9, 10, or more sequential filtrations may be required, depending on the concentration of nucleic acid and/or other components/contaminates of the initial suspension. In some embodiments, the process is repeated 6 times to achieve complete buffer replacement.

Exemplary buffering agents that may be included as part of the additional liquid include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, and/or combinations thereof.

In some embodiments, the buffering agent may be at a concentration of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.5 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 15 mM, 20 mM, or greater.

In some embodiments, the additional liquid is at least 9-fold (e.g., at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, or greater) the volume of the predetermined threshold of the retentate. For example, the volume of the additional liquid may be selected according to the volume of the filtrate to maintain an equivalent volume to be filtered as part of each sequential filtration. Accordingly, the additional liquid has a volume about equal to the difference between that of the initial suspension and the predetermined threshold. The additional liquid can be the buffer meant to replace the initial liquid (e.g., a citrate buffer, e.g., sodium citrate, e.g., 2.0 mM sodium citrate). Alternatively, the additional liquid may be adjusted during each sequential filtration step, e.g., as a step-wise progression towards the conditions of the final buffer.

The filtrate can be discarded, repurposed, or passed through the filter one or more additional times according to any of the preceding methods.

The sequential filtration and refilling steps of the present invention provide a fully automated process requiring little-to-no operator intervention. At the end of the process, the operator removes the filter housing containing the final nucleic acid suspended in the desired buffer at the desired concentration.

Apparatus

The present invention provides apparatus for concentrating nucleic acid, e.g., according to any of the preceding methods. An apparatus of the invention includes a chamber to hold a filter housing, a liquid level detector, a pressure source, and a pump. Furthermore, an apparatus may include a plurality (e.g., 1, 2, 3, 4, 5, 6, 7, 8, 9, 10, 11, 12, or more) of any one or more of the preceding elements, e.g., to filter samples in parallel. An exemplary apparatus for concentrating nucleic acid is shown holding a housing and a filtrate tube in FIG. 1.

The apparatus includes a chamber configured to hold a housing having a filter configured to hold an initial suspension of a nucleic acid in contact with the filter; a pressure source configured to releasably engage and pressurize the housing to force liquid in the initial suspension through the filter to produce a filtrate and a nucleic acid retentate; and a detector configured to detect the volume of the nucleic acid retentate and depressurize the housing upon detecting the volume reaching predetermined threshold.

The chamber can be configured to receive the housing from the operator and position it appropriately for engagement with the pressure source. Optionally, the chamber can be part of a system to move the housing into contact with the pressure source (e.g., laterally moved from the front of the apparatus to the back). A pressure cap can be included as part of the apparatus to facilitate this positioning. For example, the pressure source can feed through the pressure cap, e.g., as an integrated element, and can be displaced with the pressure cap in an upward position when the housing is being installed in the chamber. Upon installation of the housing, the pressure cap can be lowered into place over the housing to create an airtight seal around the housing. In this configuration, the pressure source is operatively connected to the inside of the housing through, e.g., a metal valve assembly or a structurally adequate tubing assembly.

Pressure Sources

The apparatus described herein include or are otherwise coupled to a pressure source (e.g., a compressed air source). In some embodiments, a separate apparatus may include the pressure supply. For example, a pressure source of the invention may be a valve assembly or conduit that connects with an external pressure source (e.g., a compressed air source).

The pressure source may be a high pressure source. For example, the pressure source may facilitate air transfer from, e.g., an air compressor, a compressed gas tank, a house gas line, or the like. In some embodiments, the pressure source may be configured to provide an inert gas (e.g., air, argon, $N_2$, or $CO_2$) to the sample container. The pressure source may be fluidically connected to a port in contact with a source of inert gas (e.g., a pressurized chamber, house gas lines, or gas cylinder). A valve assembly and/or flow meter or other pressure gauge may be used to control the amount of inert gas inputted into the apparatus. In some embodiments, one or more components or regions of the apparatus are held at positive pressure, such that suction must be applied to draw additional gas into the one or more components or regions of the apparatus. In other embodiments, one or more components or regions of the apparatus are held at negative pressure, such that the addition of gas into the one or more components or regions of the apparatus requires metering, e.g., by the valve assembly. Upon suctioning or metering of gas into a region of the apparatus, the pump may facilitate the transfer of the gas to the sample container via, e.g., a fluidic connection to an opening in the sample container (e.g., tubing, such as polyethylene tubing). Gas may be removed from a sample container via an opening in the sample container (e.g., by removing a cap, lid, or cover forming a seal at an opening) or by suction provided by a pressure source.

Alternatively, the pressure source may be a low pressure source. For example, the pressure source may be capable of providing vacuum and/or suction. Pressure sources may include one or more peristaltic pumps, syringe pumps, rotary pumps, momentum transfer pumps, diffusion pumps, scroll pumps, and/or diaphragm pumps. In some embodiments, the pressure source is a positive displacement or infusion pump such as a peristaltic pump or a syringe pump. In some embodiments, a low pressure source may include a house or central vacuum system. In other embodiments, a suction source of the invention may include a portable suction device. The pressure source may be of any useful size, pumping speed, and geometry and, if included as a component of the apparatus, may be disposed in any useful location.

Liquid Level Detectors

The apparatus includes one or more liquid level detectors to detect the level of the retentate and trigger depressurization of the housing upon reaching that level, as described above. The liquid level detector can be one sensor or a plurality, e.g., an array, of sensors. The liquid level detector can be a capacitive sensor, which can be installed on the apparatus at a position lateral to the filter, e.g., adjacent to the threshold liquid surface level, such that a liquid level drop below the threshold level triggers the sensor. Capacitive liquid level detectors are known in the art. Additionally or alternatively, other detectors or combinations of detectors can be used, including optical sensors, inductive sensors, and cameras.

Liquid Injector

In some embodiments, the apparatus further includes a liquid injector configured to inject an additional liquid into the housing. The liquid injector can be attached to a pump (e.g., a peristaltic pump, a syringe pump, a rotary pump, a momentum transfer pump, a diffusion pump, a scroll pump, or a diaphragm pump) configured to pump the additional liquid from a reservoir to the housing. For example, in some embodiments, the liquid injector is a syringe pump driven by a stepper motor with a lead screw (e.g., Hamilton PSD6).

The liquid injector can pump the additional liquid into the housing at any suitable rate. For example, the additional liquid can be injected at a rate suitable to sufficiently mix the nucleic acid suspension with the additional liquid. Further, the rate may be suitable to remove any adsorbed nucleic acid from the membrane fibers. Suitable rates of injection are about 0.1 milliliters per second (ml/s), about 0.2 ml/s, about 0.3 ml/s, about 0.4 ml/s, about 0.5 ml/s, about 1.0 ml/s, about 2.0 ml/s, about 3.0 ml/s, about 4.0 ml/s, about 5.0 ml/s, about 6.0 ml/s, about 7.0 ml/s, about 8.0 ml/s, about 9.0 ml/s, about 10 ml/s, about 15 ml/s, about 20 ml/s, about 25 ml/s, about 30 ml/s, about 35 ml/s, about 40 ml/s, about 45 ml/s, about 50 ml/s, or greater.

In some embodiments, the liquid injector is in communication with the liquid level detector. In some embodiments, the liquid injector injects the additional liquid into the housing upon detecting a volume of a nucleic acid retentate below a predetermined threshold. In some embodiments, the liquid injector is configured to inject the additional liquid into the housing after depressurization.

Reservoirs

The apparatus described herein may include one or more reservoirs for housing a liquid. A reservoir may have any useful geometry and dimensions and be formed of any useful materials. In some embodiments, the reservoir is fluidically connected to or configured to be fluidically connected to the sample container via one or more portions of tubing. In some embodiments, a valve assembly, gauge, or flow meter is disposed between the sample container and the reservoir.

The apparatus of the invention may include multiple reservoirs for housing different materials. These reservoirs may be of the same or different geometries, dimensions, and/or materials. For example, the apparatus may include a first reservoir for housing a first liquid (e.g., water, acetonitrile, acetone, or methanol) and a second reservoir for housing a second liquid, e.g., reagent, buffer, or eluting liquid. For example, a reservoir may be included as part of the invention to contain the additional liquid (e.g., a wash buffer). Additionally or alternatively, a reservoir may be a filtrate tube used to collect a filtrate. A reservoir may also be configured to collect and house waste materials.

Valve Assemblies

The apparatus described herein may include one or more valve assemblies. A valve assembly is a fluid control mechanism used to control the flow of fluids throughout the apparatus. The valve assembly includes a valve to stop, start, or throttle fluid flow. The valve assembly may include any useful valve type, including but not limited to a ball valve, diaphragm valve, and needle valve. In addition to a valve, the valve assembly may include components such as a casing, an electrical or mechanical actuation mechanism (e.g., an electric motor, a hydraulic or pneumatic component, and a solenoid) and associated components (e.g., electric connections and cables), sensors, fasteners (e.g., screws, bolts, clips, and clamps), and mechanical connectors.

A valve assembly may be fluidically connected to one or more components of an apparatus, such as a housing, an injector, a reservoir, an outlet for collection or waste, an inlet for gas, or a pump. In some embodiments, the apparatus for concentrating a nucleic acid includes a sample container, a reservoir, an inlet for inert gas, and an outlet for collection or waste, any of which may be fluidically connected to a valve assembly. A pump (e.g., a peristaltic or syringe pump) may be used to facilitate fluid transfers between components of the apparatus.

In some embodiments, the apparatus includes more than one valve assembly. For example, an apparatus may include two, three, four, five, or more valve assemblies.

Other Components

An apparatus for concentrating nucleic acid may include components in addition to those described in the preceding sections. For example, the apparatus may include one or more electrical components, cables, tubing, fasteners, connectors, containers for collection of waste or other materials, caps, lids, covers, temperature control (e.g., heating) elements, flow meters, computers, screens, casings, and housings.

In some embodiments, the apparatus includes a temperature control element. A temperature control element may include a solvent bath (e.g., a water bath), an electric heater, heating tape, a thermocouple, a sensor, a jacket, insulation, or any other useful element. In some embodiments, the apparatus includes a temperature control element that surrounds all or a portion of a housing or reservoir. For example, the housing may be wrapped with a heating element such as a heating jacket. In other embodiments, a surface or portion thereof of a housing or a filtrate tube is exposed to a heating element. For instance, any reservoir of the device may be disposed on a heatable plate or other heating element. Tubing in the apparatus may also be in contact with a heating element such as heating tape or a heating jacket.

In some embodiments, the apparatus includes one or more containers for collection of waste or other materials. These containers may be of any useful shape and dimensions and may be made of any useful materials. In some embodiments, containers for collection of waste or other materials are test tubes or vials. Containers for collection of waste or other materials may be capable of accepting any volume of liquid. In some embodiments, collection containers may be capable of accepting a volume of 1 or more ml (e.g., 1 ml, 2 ml, 5 ml, 10 ml, 15 ml, 20 ml, or more). Collection containers include at least one opening through which waste or other materials can be added and may include a cover, lid, or cap to block the opening while materials are not being added. If more than one collection container is present, the collection containers may be organized in an array, and/or a mechanism for transferring the collection containers between different areas of the apparatus may be provided. For example, a mechanical track, carousel, robotic gantry, or other mechanism may be used to position a first collection container such that it can collect materials from, e.g., the housing. After a volume of materials (e.g., waste) is added to the first collection container, the transfer mechanism can be used to move the first collection container to a different location and to position a second collection container such that it can collect materials from, e.g., the housing.

Any or all of the components described as part of the apparatus of the invention can be in communication with one another or external elements through a software and/or hardware interface, according to configurations known in the art. Software and/or hardware can be configured to allow a user to choose whether or not to inject an additional liquid, e.g., to resuspend the retentate or recover a concentrated solution of nucleic acid. Additionally or alternatively, a software and/or hardware can actuate pressurization and/or depressurization, e.g., in response to a liquid level detector. Software and/or hardware useful as part of the apparatus is known in the art.

Materials

The apparatus described herein may comprise any useful materials. For example, the housing, filters, liquid level detector, liquid injector, tubing, pressure source, valve assembly, reservoirs, and other components may include and/or be formed from any useful polymer or plastic. Such materials may include, e.g., polystyrene, polypropylene, polyvinyl chloride, or combinations thereof. Polymers and/or plastics of the invention may be composite materials in which additives to the polymers and/or plastics, such as ceramics or particles, alter the mechanical properties.

Elements of the invention may also include and/or be formed from glass. For example, an apparatus of the invention may include a reservoir made wholly or partially from glass.

In some embodiments, the liquid level detector, liquid injector, tubing, pressure source, valve assembly, reservoirs, and other components may include and/or be formed from any useful metal or metal alloy, e.g., stainless steel or aluminum.

Compositions

The invention further provides a filtered nucleic acid suspension produced by methods and apparatus described herein. Such nucleic acid suspensions can be further processed according to known methods, e.g., into pharmaceutical compositions. For example, nucleic acid suspensions provided by the present invention can be mixed with pharmaceutically acceptable excipients or one or more additional active substances, e.g., therapeutically and/or prophylactically active substances. General considerations in the formulation and/or manufacture of pharmaceutical agents may be found, for example, in Remington (The Science and Practice of Pharmacy, 22nd Edition, A. R. Gennaro, Lippincott, Williams & Wilkins, Baltimore, MD, 2012).

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

EXAMPLES

Example 1: Automated Concentration or Solvent Exchange Using an Apparatus of the Invention Operation of the apparatus begins with preparation of an initial nucleic acid suspension in each of six EMD Millipore Amicon 15 filter housings containing a 30,000 MWCO filter. 13.0 mL of a 100 µg/ml mRNA suspension is placed in a filter housing positioned within a 50 mL filtrate tube to receive the filtrate as it passes through the filter. Each housing and filtrate tube are loaded within a chamber to hold the housing in place within the apparatus.

Next, the apparatus pulls the six housings under pressure caps, and the pressure caps lower to engage the housings with the pressure source. The pressure source is activated upon confirmation by a sensor and injects air into the housing, pressurizing the housing to 7 bar and forcing the liquid in the initial nucleic acid suspension, but not the mRNA molecules, through the filter and into the filtrate tube.

Capacitive liquid level detectors are attached at the apparatus laterally at each of the filters. As the liquid level of the suspension in all six of the housings drops to a height corresponding to 1.0 mL or less, the capacitive liquid level sensors actuate depressurization of the housing by opening a valve.

After depressurization, the pressure caps lift from the housings, and the housings are ejected from the apparatus to complete the nucleic acid concentration protocol. If complete solvent exchange is required, the housings remain in the system, and a pump refills the filter housing by adding 12.5 mL of 2 mM sodium citrate. The process is automatically repeated five additional times for a total of six cycles, at which point the osmolality of the nucleic acid suspension has stabilized and buffer replacement is complete. After completion of six cycles, the pressure caps lift from the housings, and the housings are ejected from the system.

OTHER EMBODIMENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

What is claimed is:

1. An apparatus for concentrating nucleic acid, the apparatus comprising:
   a) a chamber comprising a housing having a filter configured to hold an initial suspension comprising nucleic acid in contact with the filter;
   b) a pressure source configured to releasably engage and pressurize the housing to force liquid in the initial suspension through the filter to produce a filtrate and a nucleic acid retentate;
   c) a pressure cap configured to engage the housing with the pressure source;
   d) a detector configured to detect the volume of the nucleic acid retentate and depressurize the housing upon detecting the volume reaching a predetermined threshold;
   e) a liquid injector configured to inject an additional liquid into the housing;
   f) a pump that is connected to the liquid injector and a liquid reservoir; and
   g) a processor that:
      i) is in communication with the detector;
      ii) causes the pressure source to depressurize and lift the pressure cap from the housing upon receiving a signal from the detector indicating a reduction in the volume of the nucleic acid retentate beneath a predetermined threshold; and
      iii) causes the pump to automatically inject additional liquid from the liquid reservoir, through the injector, and into the housing upon receiving the signal from the detector indicating the reduction in the volume of the nucleic acid retentate beneath the predetermined threshold and upon the pressure cap being lifted.

2. The apparatus of claim 1, wherein the chamber is configured to receive the housing provided by a user and position the housing for engagement with the pressure source.

3. The apparatus of claim 1, wherein the pressure source is configured to inject a gas into the housing.

4. The apparatus of claim 1, wherein the detector is a capacitive liquid level detector.

5. The apparatus of claim 1, wherein the liquid injector is configured to inject the additional liquid into the housing after depressurization of the housing.

6. The apparatus of claim 1, wherein the liquid injector adds the additional liquid into the housing at a rate suitable to sufficiently mix the suspension with the additional liquid.

7. The apparatus of claim 1, wherein the liquid injector adds the additional liquid at a rate suitable to remove adsorbed nucleic acid from membrane fibers of the filter.

8. The apparatus of claim 1, wherein the liquid injector is attached to a pump.

* * * * *